United States Patent [19]

McCauley et al.

[11] Patent Number: 5,470,865
[45] Date of Patent: Nov. 28, 1995

[54] PHARMACEUTICAL COMPOSITION

[75] Inventors: Mary K. McCauley, Lafayette; Kenneth P. Moder, West Lafayette; Jeffrey L. Speakman, Romney, all of Ind.

[73] Assignee: Eli Lilly and Company, Indianapolis, Ind.

[21] Appl. No.: 298,486

[22] Filed: Aug. 30, 1994

[51] Int. Cl.$^6$ .................................................. A01N 43/78
[52] U.S. Cl. ................................................................ 514/365
[58] Field of Search ................................................ 514/365

[56] References Cited

U.S. PATENT DOCUMENTS

| | | | |
|---|---|---|---|
| 4,375,547 | 3/1983 | Pioch | 548/205 |
| 4,382,090 | 5/1983 | Pioch | 424/270 |
| 4,587,344 | 5/1986 | Ryan | 548/205 |
| 4,760,075 | 7/1988 | Pioch | 514/365 |
| 4,777,260 | 10/1988 | Ryan | 548/205 |
| 4,904,792 | 2/1990 | Pioch | 548/205 |
| 5,334,725 | 8/1994 | Moder | 548/147 |

FOREIGN PATENT DOCUMENTS

| | | |
|---|---|---|
| 285681 | 10/1988 | European Pat. Off. . |
| 396830 | 11/1990 | European Pat. Off. . |
| 459695 | 12/1991 | European Pat. Off. . |
| 492247 | 7/1992 | European Pat. Off. . |
| 2038922 | 1/1993 | Spain . |
| 9421239 | 2/1994 | WIPO . |

OTHER PUBLICATIONS

Suzuki, H. et al., Yakuci to Chiryo (1993), 21 (12) 4581–4589.
Caballeria, J. et al., Dig. Dis Sei (1991) 36 (12) 1673–1679.
Palmer, R. et al., Am. J. Gastroenternal (1991) 86 (12), 1749–1755.

*Primary Examiner*—Paul J. Killos
*Attorney, Agent, or Firm*—Martin A. Hay; Robert A. Conrad; David E. Boone

[57] ABSTRACT

The present invention provides an odorless pharmaceutical composition of nizatidine. It also provides a novel form of nizatidine and a process for the preparation of this form.

17 Claims, No Drawings

PHARMACEUTICAL COMPOSITION

FIELD OF THE INVENTION

The present invention relates to pharmaceuticals. More particularly it relates to a new pharmaceutical composition of the drug nizatidine. It also relates to a new form of nizatidine and to a process for the preparation of this form.

BACKGROUND OF THE INVENTION

All drugs contain various levels of related substances in addition to the active ingredient. The identities and amounts of the related substances depend upon the way in which the drug has been manufactured. Thus different manufacturing processes afford different forms of a drug.

Nizatidine is the generic name for a drug the active ingredient of which is N-[2-[[[2-[dimethylamino)methyl]-4-thiazolyl]methyl]thio]ethyl-N'-methyl-2-nitro-1,1-ethenediamine. The compound is a histamine $H_2$-receptor antagonist which is used in the treatment of duodenal ulcers and other gastrointestinal disorders.

Processes for preparing nizatidine have been disclosed in U.S. Pat. Nos. 4,587,344, 4,777,260; 4,904,792 and 5,334,725. These processes all involve compounds which produce strong and unpleasant odors. The final stages of the processes disclosed in U.S. Pat. Nos. 4,904,792 and 5,334,725 both involve the same reaction of 2-(2-dimethylaminomethyl-4-thiazolylmethylthio)ethylamine with N-methyl-1-methylthio-2-nitroethyleneamine. The examples illustrate the use of water as reaction solvent. The final stage of the process disclosed in U.S. Pat. No. 4,587,344 involves the reaction of N-methyl-S-methyl-N'-[2-(2-dimethylaminomethylthiazol- 4-ylmethylthio)ethyl isothiourea with nitromethane. Each of the final stages of the processes disclosed in U.S. Pat. Nos. 4,904,272, 5,334,725 and 4,857,344 involves the production of methanethiol, which has a particularly unpleasant sulfur-like odor. The final stage of the process disclosed in U.S. Pat. No. 4,777,260 involves the reaction of N-[2-[[[2-(dimethylamino)-methyl]-4-thiazolyl] methyl]thio]ethyl-2-nitro-1-phenoxy-1-etheneamine with methylamine. This reaction does not involve the formation of methanethiol.

It will be appreciated that each of the forms of nizatidine prepared by each of the different processes is different, because of the different residual substances present.

Pharmaceutical compositions of nizatidine are presently sold in gelatin capsules under the trade mark AXID (AXID is a registered trademark of Eli Lilly and Company). The capsules emit a characteristic sulfur-like odor. This odor is referred to in package inserts accompanying the capsules and also in physicians manuals, for example the Physician's Desk Reference, 48th Edition, 1994, page 1208, published by Medical Economics Data Production Company at Montvale, N.J. 07645-1742, United States.

It has now been found that the source of the odor of the commercially available gelatin capsules containing nizatidine is not the active ingredient, but a trace related substance in the drug, N-methyl-1-methylthio-2-nitroethyleneamine. This is one of the starting materials in the process for preparing nizatidine disclosed in U.S. Pat. Nos. 4,904,792 and 5,344,725. The nizatidine present in the commercial formulation has been found typically to contain about 150 ppm of this related substance.

It has also been found that N-methyl-1-methylthio-2-nitroethyleneamine may be removed from nizatidine containing N-methyl-1-methylthio-2-nitroethyleneamine by heating said nizatidine containing N-methyl-1-methylthio-2-nitroethyleneamine in water at an elevated temperature.

Without wishing to be bound by theory, it is believed that the odor of the commercially available gelatin capsules results from a reaction, catalysed by the active ingredient, between N-methyl-1-methylthio-2-nitroethyleneamine and water present inside the capsule. The reaction affords methanethiol, which oxidises in air to afford dimethyldisulfide, and it is this substance that is responsible for the odor.

SUMMARY OF THE INVENTION

The present invention provides a pharmaceutical composition of nizatidine in which the nizatidine has been heated in the presence of water to remove N-methyl-1-methylthio-2-nitroethyleneamine. It also provides a process for preparing a form of nizatidine, which comprises heating nizatidine containing N-methyl-1-methylthio-2-nitroethyleneamine in the presence of water to remove said N-methyl-1-methylthio-2-nitroethyleneamine, and to the form of nizatidine so prepared.

DETAILED DESCRIPTION OF THE INVENTION

The present invention provides an odorless pharmaceutical composition of nizatidine which is characterized in that the nizatidine is a form of nizatidine that is obtained from nizatidine containing N-methyl-1-methylthio-2-nitroethyleneamine by a process which comprises the step of heating said nizatidine containing N-methyl-1-methylthio-2-nitroethyleneamine in the presence of water to remove said N-methyl-l-methylthio-2-nitroethyleneamine.

The pharmaceutical composition according to the invention may be formulated in conventional manner, and includes tablets, chewable tablets, capsules, solutions, parenteral solutions, intranasal sprays or powders, troches, suppositories, transdermal patches and suspensions. In general, compositions contain from about 0.5% to about 50% by weight of nizatidine in total, depending on the desired doses and the type of composition to be used. The amount of nizatidine, however, is best defined as the effective amount, that is, the amount of nizatidine which provides the desired dose to the patient in need of such treatment.

Capsules are prepared by mixing nizatidine with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the nizatidine. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking n the die. The lubricant is chosen from such slippery solids as talc, magnesium and calcium stearate, stearic acid and hydrogenated vegetable oils.

Tablet disintegrators are substances which swell when wetted to break up the tablet and release the active ingredient. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form which a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. It is preferred to formulate the new form of nizatidine as an enteric composition, and even more preferred to formulate it as an enteric pellet.

Tablets are often coated with sugar as a flavor and sealant, or with film-forming protecting agents to modify the dissolution properties of the tablet. The nizatidine may also be formulated as chewable tablets, by using large amounts of pleasant-tasting substances such as mannitol in the formulation, as is now well-established practice. Instantly dissolving tablet-like formulations such as effervescent tablet formulations are also now frequently used to assure that the patient consumes the dosage form, and to avoid the difficulty in swallowing solid objects that bothers some patients.

When it is desired to administer the active ingredient as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It has been found that the odor emitted from solutions of commercial nizatidine are particularly strong and unpleasant. Accordingly, pharmaceutical compositions according to the invention which are aqueous solutions or effervescent tablet formulations are particularly advantageous embodiments of the invention.

Nizatidine which has been prepared by reacting 2-(2-dimethylaminomethyl-4-thiazolylmethylthio)ethylamine with N-methyl-1-methylthio-2-nitroethyleneamine, the process described in U.S. Pat Nos. 4,904,792 and 5,334,725, has been found to contain two related substances in addition to N-methyl-1-methylthio-2-nitroethyleneamine. These are N,N'-bis[2-[[[2-[2-(dimethylamino)methyl]-4-thiazole]methyl]thio]ethyl]- 2-nitro-1,1-ethenediamine and N,N'-dimethyl-2-nitro-1,1-ethenediamine. It has been found that these two related substances are not removed when nizatidine containing them is converted into the new form by heating in the presence of water.

According to another aspect therefore, the present invention provides a pharmaceutical composition of nizatidine in which the nizatidine is in a form that contains N,N'-bis[2-[ [[2-[2-(dimethylamino)-methyl]-4-thiazole]methyl]-thio] ethyl]- 2-nitro-1,1-ethenediamine and N,N'-dimethyl-2-nitro-1,1-ethenediamine, but not N-methyl-1-methylthio-2-nitroethyleneamine.

According to yet another aspect, the invention provides a process for preparing a form of nizatine, which comprises heating nizatidine containing N-methyl-1-methylthio-2-nitroethyleneamine in the presence of water to remove said N-methyl-1-methylthio-2-nitroethyleneamine.

The length of time required to remove the N-methyl-1-methylthio-2-nitroethyleneamine by the process according to the invention depends upon the conditions under which the process is conducted and the amount of N-methyl-1-methylthio-2-nitroethyleneamine that the nizatidine starting material contains. The time taken for the conversion of the nizatidine containing N-methyl-1-methylthio-2-nitroethyleneamine into the new form is typically in the range of from 2 to 24 hours. When the process is performed according to the preferred reaction conditions described hereinafter, the conversion is commonly completed within 4 to 20 hours, typically within 6 to 12 hours.

It has been found that the presence of an organic solvent, such as acetone, retards the conversion of the nizatidine containing N-methyl-1-methylthio-2-nitroethyleneamine into the new form. Accordingly the reaction is preferably performed in water.

Preferably the nizatidine containing N-methyl-1-methylthio-2-nitroethyleneamine is heated at a temperature in the range of from 70° to 110° C., more preferably at a temperature in the range of from 90° to 105° C. Most preferably it is heated under reflux.

The nizatidine containing N-methyl-1-methylthio-2-nitroethyleneamine is preferably heated in the presence of from 0.3 to 2.0 liters of water per kg of nizatidine, preferably from 0.45 to 0.55 liters, especially about 0.5 liters. When the amount of water used per kg of nizatidine containing N-methyl-1-methylthio-2-nitroethyleneamine is within this range, the nizatidine should be able to be completely dissolved in the water, which is advantageous. If an organic solvent is present with the nizatidine starting material, as in a wet filter cake, this is preferably removed by distillation during the performance of the process.

The nizatidine used in the process according to the invention may conveniently contain N-methyl-1-methylthio-2-nitroethyleneamine in an amount up to 5,000 p pm. Preferably it contains up to 2,000 ppm of the substance, for example from 40 to 1,500 ppm.

It will be appreciated that the nizatidine containing N-methyl-1-methylthio-2-nitroethyleneamine which is used as the starting material in the process according to the invention may or may not be in a pharmaceutically acceptable state of purity. Accordingly, it may be necessary and/or desirable to perform one or more purification steps, such as a carbon treatment step or a crystallisation step, during or after the step of heating the nizatidine containing N-methyl-1-methylthio-2-nitroethyleneamine in the presence of water. The process according to the invention includes all such steps.

The heating step is preferably followed by a crystallization step. Preferably the crystallization is performed using a solvent selected from acetone, ethanol, water and mixtures thereof. A particularly preferred solvent is a mixture of acetone and water. Conveniently, after the nizatidine containing N-methyl-1-methylthio-2-nitroethyleneamine has been heated in water, the resultant solution is cooled and acetone is added to induce crystallization.

Particular advantages of the process according to the invention are that the new form of nizatidine is obtained in high yield, and that the amounts of related substances are not increased.

The form of nizatidine prepared by the process according to the invention is believed to be novel, and accordingly forms a further aspect of the invention.

According to yet another aspect, the invention provides a form of nizatidine that contains N,N'-bis[2-[[[2-[2-(dimethylamino)methyl]-4-thiazole]methyl]thio]ethyl]-2-nitro-1,1-ethenediamine and N,N'-dimethyl-2-nitro-1,1-ethenediamine, but not N-methyl-1-methylthio-2-nitroethyleneamine.

The following Examples illustrate the invention:

EXAMPLE 1

Preparation of New Form of Nizatidine

Nizatidine (30 grams) containing N,N'-bis[2-[[[2-[2-(dimethylamino)methyl]-4-thiazole]methyl]thio]ethyl]-2-nitro-1,1-ethenediamine, N,N'-dimethyl-2-nitro-1,1-ethenediamine and 1182 ppm of N-methyl-1-methylthio-2-nitroethyleneamine and water (14.4 grams) were combined in a suitable flask (100 ml) equipped with a condenser. The contents of the flask were heated to 100° C. Initially, the mixture was not stirrable. Dissolution occurred at approximately 50°–60° C. at which time agitation was started. The contents were stirred at 97° to 102° C. for 7 hours. The contents were then allowed to cool to approximately 80° C. and were transferred to a suitable crystallization flask (500 ml). The treatment flask was then rinsed with two portions of acetone (50 ml each) and the rinses were added to the crystallization flask. Acetone (100 ml) was then added to the crystallization flask (total acetone added: 200 ml). The contents were allowed to stir at room temperature for 1 hour. The flask was then cooled to 0° C. for 1 hour. The flask was then cooled to −10° to −5° C. with an ice/acetone bath and allowed to stir for 3 hours. The crystals were isolated by filtration. The flask was rinsed with acetone pre-chilled to −10° to −5° C. (50 ml), which is then used to wash the isolated crystals. The crystals were washed again with acetone pre-chilled to −10° to −5° C. (50 ml). The crystals were then dried in a vacuum oven at 60° C. overnight. The product was found to contain N,N'-bis[2-[[[2-[2--(dimethylamino)methyl]-4-thiazole]methyl]thio]ethyl]-2-nitro-1,1-ethenediamine and N,N'-dimethyl-2-nitro-1,1-ethenediamine, but no detectable amount of N-methyl-1-methylthio-2-nitroethyleneamine.

The non-odor producing property of the nizatidine prepared by the process described hereinabove may be demonstrated by the following test method.

0.75 grams of nizatidine is added to a 22 ml headspace vial (Perkin Elmer). To the nizatidine is added 10 ml of water. The vial is capped with a crimp top cap. The cap has a butyl rubber septum which is coated on one side with PTFE. The sealed vial is stored in an oven at 60° C. for approximately 24 hours. An hour or two after preparation, the vial is shaken to complete dissolution. After 24 hours, the vial may be opened with the odor readily detectable. Alternately, the contents of the vial may be subjected to purge and trap/GC/MS analysis.

N-methyl-1-methylthio-2-nitroethyleneamine in nizatidine will degrade in the presence of water and give off methanethiol in the process. Methanethiol readily dimerizes to dimethyldisulfide, and it is dimethyldisulfide that is measured in this method.

A suitable carrier gas is used to continuously purge through the content of the vial for a period of 11 minutes the volatile organics are trapped on a sorbent trap in the purge & trap instrument. At the time of analysis, the trap quickly heats up, and the trapped organics are desorbed and pass into the gas chromatograph. The rest of the method is a typical GC/MS analysis. 2-bromo-1-chloropropane is used as the internal standard.

Specific Conditions:

Instruments:

Purge and Trap: Tekmar LSC 2000 Tekmar model 4000; trap containing Tenax (TM) and silica gel; Connection to GC through a heated transfer line.

Gas Chromatograph/Mass Spectrometer: VG Trio-2, equipped with a jet separator interface.

Chromatographic column: 6 ft×2 mm ID glass column packed with 1% SP-1000 on Carbopack B, 60/80 mesh pr Supelco, Inc.

Conditions:

Purge and Trap:
 Purge flow: 20 ml/minute
 Purge time: 11.0 minutes
 Desorb temperature: 180° C. max.
 Desorb time: 3–6 minutes GC/MS:
 Electron energy: 70 volts (nominal)
 Mass range: 47–280
 Scan Time: 2 scans/sec.
 Source temp: 200° C.
 GC temp profile: 35° C., hold 5 min; ramp to 220° C. @ 8°/min; hold 10 min.
 Injector temp: 180° C.
 Carrier Gas: Helium

EXAMPLE 2

(a) Aqueous formulation of Nizatidine

| Ingredient | % w/v |
| --- | --- |
| Nizatidine | 1.50 |
| Water + Sodium phosphate tribasic, 12 hydrate + Potassium phosphate dibasic pH = approx. 8.5 | 15.0 |
| Benzyl alcohol NF | 0.120 |
| Methylparaben NF | 0.100 |
| Propylparaben NF | 0.0500 |
| Glycerin, 99% USP | 14.0 |
| Fructose 95 | 25.0 |
| Sucrose, Beet USP | 32.0 |
| Prosweet G Blend of Proprietory sweeteners | 2.00 |
| Sodium Saccharin | 0.250 |
| Sorbitol USP qs ad | 100% vol. |

The buffer is heated to either 72° C. or 100° C. and nizatidine is dissolved in the buffer. The solutions are heated for specific times and then added to the main batch (the sugar base).

(b) Lipid formulation of Nizatidine

| Ingredient | % w/v |
|---|---|
| Nizatidine | 1.50 |
| Confectioners Sugar NF | 25.0 |
| Colloidal Silicon Dioxide | 1.00 |
| Magnasweet 135 B | 1.00 |
| Aspartame | 1.00 |
| Medium Chain Triglyceride | QS |

Powders are dry blended and added to a medium chain triglyceride and mixed well. The mixture is then passed through a colloid mill to reduce particle size.

(c) Capsule formulation Of Nizatidine

| | Mg./Capsule | |
|---|---|---|
| | 150 Mg. | 300 Mg. |
| Nizatidine | 151.50 | 303.00 |
| (1% excess for manufacturing loss) | | |
| Starch Powder | 10.75 | 5.38 |
| (Includes excess for moisture loss) | (0.75) | (0.38) |
| Starch Flowable | 97.30 | 16.13 |
| (Includes excess for moisture loss) | (6.81) | (1.13) |
| Povidone | — | 15.00 |

The 150 Mg. formula is granulated with Purified Water. The 300 Mg. formula is granulated with an aqueous Povidone solution. Both granulations are dried in a fluidized-bed dryer and dry sized. The sized granulation is then blended with:

| | | |
|---|---|---|
| Starch Flowable with Silicone 10% | 26.00 | — |
| Starch Flowable | 10.10 | — |
| Magnesium Stearate | 2.00 | — |
| Starch Powder | 37.91 | 17.55 |
| CMC Sodium Cross-linked (Croscarmellose sodium, NF) | — | 8.00 |
| Silicone Fluid | — | 7.20 |
| Talc | — | 9.25 |
| Fill Weight | 328.00 | 380.00 |
| Capsule size | 2 | 1 |

We claim:

1. A pharmaceutical composition of nizatidine, in which the nizatidine has been heated in the presence of water to remove N-methyl-1-methylthio-2-nitroethyleneamine.

2. A pharmaceutical composition as claimed in claim 1, which is an aqueous solution or an effervescent tablet.

3. A pharmaceutical composition of nizatidine, in which the nizatidine is in a form which contains N,N'-bis[2-[[[2-[2-(dimethylamino)methyl]-4-thiazole]methyl]thio]ethyl]-2-nitro-1,1-ethenediamine and N,N'-dimethyl-2-nitro-1,1-ethenediamine, but not N-methyl-1-methylthio-2-nitroethyleneamine.

4. A pharmaceutical composition as claimed in claim 3, which is an aqueous solution or an effervescent tablet.

5. A process for preparing a form of nizatidine, which comprises heating nizatidine containing N-methyl-1-methylthio-2-nitroethyleneamine in the presence of water to remove said N-methyl-1-methylthio-2-nitroethyleneamine.

6. A process as claimed in claim 5, in which the nizatidine containing N-methyl-1-methylthio-2-nitroethyleneamine is heated in water.

7. A process as claimed in claim 6, in which the nizatidine containing N-methyl-1-methylthio-2-nitroethyleneamine is heated in from 0.3 to 2.0 liters of water per kilogram of nizatidine.

8. A process as claimed in claim 7, in which the number of liters of water per kilogram of nizatidine is in the range of from 0.45 to 0.55.

9. A process as claimed in claim 5, in which the nizatidine is heated at a temperature in the range of from 70° to 110° C.

10. A process as claimed in claim 9 in which the nizatidine is heated at a temperature in the range of from 90° to 105° C.

11. A process as claimed in claim 10, in which the nizatidine is heated under reflux.

12. A process as claimed in claim 5, in which the nizatidine contains N-methyl-1-methylthio-2-nitroethyleneamine in an amount up to 5,000 ppm.

13. A process as claimed in claim 12, in which the nizatidine contains from 40 to 1,500 ppm of N-methyl-1-methylthio-2-nitroethyleneamine.

14. A process as claimed in claim 5, which further comprises the step of crystallised out the form of nizatidine.

15. A process as claimed in claim 14, in which the form of nizatidine is crystallised out using a solvent selected from acetone, ethanol, water and mixtures thereof.

16. The form of nizatidine prepared by the process of claim 5.

17. A form of nizatidine which contains N,N'-bis[2-[[[2-[2-(dimethylamino)methyl]- 4-thiazole]methyl]thio]ethyl]-2-nitro-1,1-ethenediamine and N,N'-dimethyl-2-nitro-1,1-ethenediamine, but not N-methyl-1-methylthio-2-nitroethyleneamine.

* * * * *

UNITED STATES PATENT AND TRADEMARK OFFICE
CERTIFICATE OF CORRECTION

PATENT NO.    :   5,470,865

DATED         :   November 28, 1995

INVENTOR(S)   :   Mary K. McCauley, et al.

It is certified that an error appears in the above-identified patent and that said Letters Patent is hereby corrected as shown below:

In claim 14 the word "crystallised" should be changed to "crystallising".

Claim 14 reads:

"A process as claimed in claim 5, which further comprises the step of crystallised out the form of nizatidine."

and should read:

"A process as claimed in claim 5, which further comprises the step of crystallising out the form of nizatidine."

Signed and Sealed this

Twenty-seventh Day of May, 1997

Attest:

*Attesting Officer*

BRUCE LEHMAN

*Commissioner of Patents and Trademarks*